(12) United States Patent
Yatsuo

(10) Patent No.: US 10,996,295 B1
(45) Date of Patent: May 4, 2021

(54) NOISE GENERATION SOURCE SEARCH DEVICE AND NOISE GENERATION SOURCE SEARCH METHOD

(71) Applicant: HITACHI, LTD., Tokyo (JP)

(72) Inventor: Takeshi Yatsuo, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/636,116

(22) PCT Filed: Aug. 3, 2018

(86) PCT No.: PCT/JP2018/029297
§ 371 (c)(1),
(2) Date: Feb. 3, 2020

(87) PCT Pub. No.: WO2019/073674
PCT Pub. Date: Apr. 18, 2019

(30) Foreign Application Priority Data

Oct. 12, 2017 (JP) .............................. JP2017-198745

(51) Int. Cl.
*G01R 33/36* (2006.01)
*G01R 33/385* (2006.01)

(52) U.S. Cl.
CPC ..... *G01R 33/3621* (2013.01); *G01R 33/3607* (2013.01); *G01R 33/385* (2013.01)

(58) Field of Classification Search
CPC .............. G01R 33/3621; G01R 33/385; G01R 33/3607
See application file for complete search history.

(56) References Cited

U.S. PATENT DOCUMENTS 6,580,915 B1 * 6/2003 Kroll ..................... G01S 5/14
455/279.1

FOREIGN PATENT DOCUMENTS

| JP | H6-50606 U | 7/1994 |
| JP | 2002-291715 A | 10/2002 |
| JP | 2002-323548 A | 11/2002 |
| JP | 2011-053055 A | 3/2011 |
| JP | 2011-104134 A | 6/2011 |

OTHER PUBLICATIONS

International Search Report, dated Nov. 6, 2018, which issued during the prosecution of International Application No. PCT/JP2018/029297, which corresponds to the present application.

* cited by examiner

*Primary Examiner* — G. M. A Hyder
(74) *Attorney, Agent, or Firm* — Baker Botts L.L.P.

(57) ABSTRACT

Provided is a noise source search device to be applied to an MM apparatus that obtains an NMR signal generated from a subject disposed in a static magnetic field by applying an RF pulse of a high frequency coil and a gradient magnetic field pulse of a gradient magnetic field coil to the subject, the device including: a reference antenna and a probe antenna that measure a noise generated in the MRI apparatus; a noise generation condition specification unit that specifies an axis and a drive frequency as a noise generation condition generated in the MRI apparatus, on the basis of a noise intensity of the noise that is measured by the reference antenna; and a noise generation site specification unit that drives the gradient magnetic field coil under the noise generation condition that is specified by the noise generation condition specification unit.

13 Claims, 17 Drawing Sheets

FIG. 13
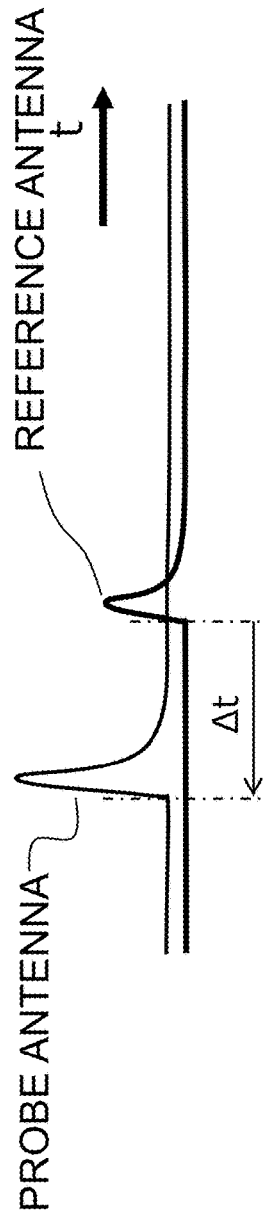
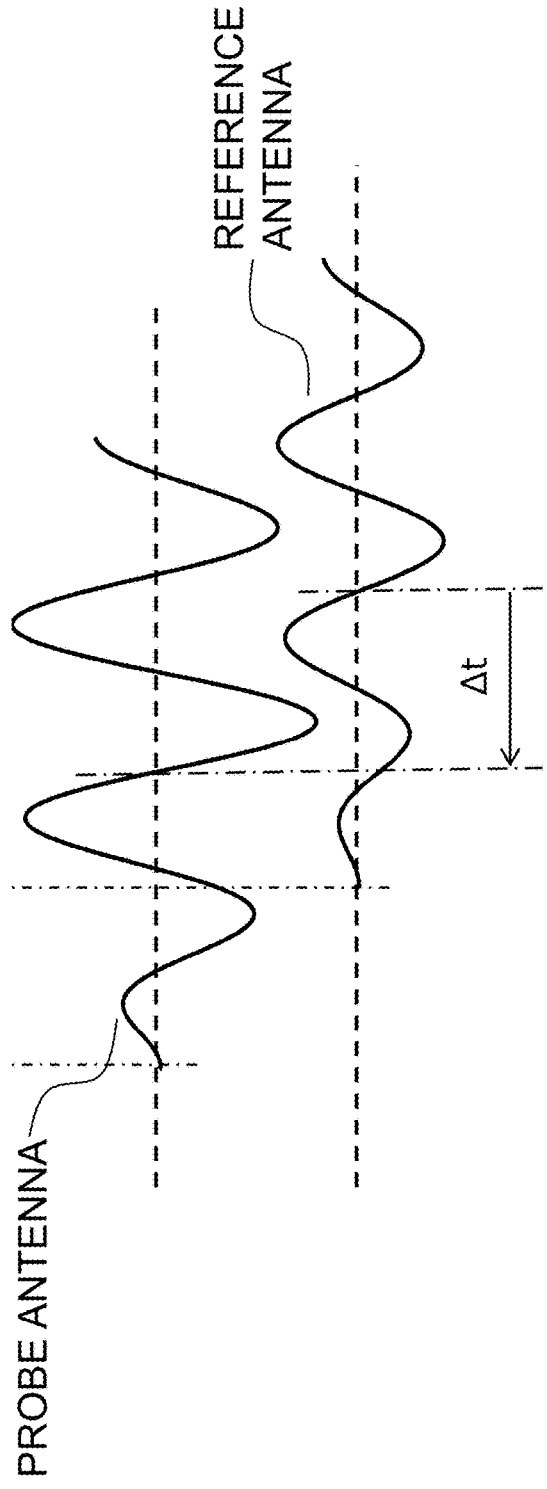

ACTUAL SPACE IMAGE

SIGNAL MAINLY FORMING IMAGE

SHOT NOISE SIGNAL k SPACE DATA

NOISE GENERATION SOURCE SEARCH DEVICE AND NOISE GENERATION SOURCE SEARCH METHOD

TECHNICAL FIELD

The present invention relates to a noise generation source search device and a noise generation source search method that are applied to a magnetic resonance imaging apparatus (hereinafter, referred to as an "MRI apparatus"), and search a generation source of the noise generated in the MRI apparatus.

BACKGROUND ART

In the related art, an MRI apparatus is known in which in a state where a subject (in particular, a human body) is disposed in a homogeneous static magnetic field, a nuclear magnetic resonance (NMR) signal generated by applying a high frequency magnetic field (RF) pulse to the subject is measured, and the form or the function of the head, the abdominal part, the four extremities, and the like of the subject is two-dimensionally or three-dimensionally imaged. In the MRI apparatus, the NMR signal is frequency-encoded as phase encoding different in accordance with a gradient magnetic field is applied, and is measured as time-series data, the measured NMR signal is subjected to two-dimensional or three-dimensional Fourier transform, and thus, is reconfigured as an image.

However, the NMR signal has an amplitude smaller than that of an electromagnetic wave that propagates through the air, and thus, the electromagnetic wave generated from a radio, a television, a mobile phone, a motor, a switch, and the like becomes a noise. For this reason, the MRI apparatus is provided in an electromagnetic wave shield room configured of a material having high conductivity, such as a copper foil, and thus, an external noise source and the MRI apparatus are isolated from each other, and the electromagnetic wave that arrives at the MRI apparatus from the outside the electromagnetic wave shield room is shielded.

On the other hand, in the MRI apparatus, there is a case where a noise such as a "shot noise" or a "spike noise" is generated at the time of photographing, in addition to such an electromagnetic noise. Such a noise indicates a case where in the MRI apparatus, a noise exists in the shape of a dot, in data on a k space. In FIG. 17A, an example of the shot noise is illustrated. For example, a k space of which a horizontal axis is set to time and a vertical axis is set to a phase encoding direction is filled with the NMR signal measured at the time of photographing by changing a phase encoding gradient magnetic field, but there is a case where a shot noise in the shape of a dot exists in addition to data configuring a subject image, in k space data. As described above, in a case where data including the shot noise illustrated in FIG. 17A is imaged by being subjected to Fourier transform, as illustrated in FIG. 17B, a pattern in the shape of a diagonal net is generated. The pattern is different in accordance with the position of a shot noise signal and the number of shot noise signals, it is difficult to uniformly represent the properties of the noise, but there are many cases where geometric pattern is seen in the background that originally has no signal.

The cause of such noise generation can be divided into several types of patterns. Noise generation due to a contact between metals is most considered. In particular, a potential is generated at the moment when heterologous metals are in contact with each other by a piezoelectric effect, and thus, the contact between the heterologous metals causes partial discharge, and becomes a noise source. In addition, similarly, a contact between two metal members in locations having different potentials also generates a noise. In addition, a contact failure in an electric circuit is considered. In a case where there is a connector with a loose contact, a track, a device, and the like, in the circuit, a connection state is changed in accordance with the vibration of a gradient magnetic field coil, and thus, a noise synchronized with the drive of the gradient magnetic field coil can be generated.

In addition, static electricity can also be a noise source. For example, in a case where heterologous resin members are rubbed with each other or ripped from each other, in a manner that depends on the drive of the gradient magnetic field coil, one of the heterologous resin members is electrified, there is a case where discharge is performed in the middle of the repetition, and static electricity is generated.

As described above, in many cases, a physical vibration of the gradient magnetic field coil, a freezing machine, or the like propagates through a problematic site, and finally, a noise is generated.

In a case where such a noise affects an image, it is necessary to specify a noise source, to perform correction, and to acquire an image in which a noise is reduced. Therefore, for example, in Patent Document 1, a noise generation site specification device that drives a power system and a transmission system of the MRI apparatus by switching, and thus, specifies a unit that is a noise source is disclosed as a technology for searching the noise source in the MRI apparatus.

CITATION LIST

Patent Document

Patent Document 1: JP-A-2002-291715

SUMMARY OF THE INVENTION

Technical Problem

However, in the noise generation site specification device of Patent Document 1 described above, it is only possible to specify the unit that is the noise source in the power system and the transmission system, but it is not possible to obtain information with respect to a detailed noise source. For example, in a case where a noise is generated due to the conveyance of the vibration of the gradient magnetic field coil, the drive of the gradient magnetic field coil is the cause of the noise generation, and a generation site of the noise is not the gradient magnetic field coil, but the noise may be generated from any of the surrounding structures. In this case, it is necessary to specifically specify a site in the structures in which the noise is generated, but in the noise generation site specification device of Patent Document 1, it is not possible to obtain the detailed information.

In a case where it is not possible to accurately specify the noise source and the noise generation site, it is not possible to suitably reduce the noise, and thus, image quality of an image to be acquired in the MRI apparatus decreases.

The invention has been made in consideration of such circumstances described above, and an object thereof is to accurately specify the generation site in an MRI apparatus.

Solution to Problem

In order to attain the object, the invention provides the following means.

One aspect of the invention provides a noise source search device to be applied to an MRI apparatus that obtains an NMR signal generated from a subject disposed in a static magnetic field by applying an RF pulse of a high frequency coil and a gradient magnetic field pulse of a gradient magnetic field coil to the subject, the device including: a reference antenna and a probe antenna that measure a noise generated in the MRI apparatus; a noise generation condition specification unit that specifies a noise generation condition generated in the MRI apparatus, on the basis of a noise intensity of the noise that is measured by the reference antenna; and a noise generation site specification unit that measures a noise generated under the noise generation condition that is specified by the noise generation condition specification unit, with the reference antenna and the probe antenna disposed in a position different from that of the reference antenna, and specifies a noise generation site in the MRI apparatus, on the basis of a measurement time difference in the noise that is measured by the reference antenna and the probe antenna.

In addition, another aspect of the invention provides a noise source search method to be applied to an MRI apparatus that obtains an NMR signal generated from a subject disposed in a static magnetic field by applying an RF pulse of a high frequency coil and a gradient magnetic field pulse of a gradient magnetic field coil to the subject, the method including: a noise generation condition specification step of measuring a noise generated from the MRI apparatus, and of specifying an axis and a drive frequency of the gradient magnetic field coil as a noise generation condition, on the basis of a noise intensity of the measured noise; a step of measuring the noise generated from the MRI apparatus in a plurality of sites that are different from each other; a noise generation site specification step of driving the gradient magnetic field coil, in accordance with the noise generation condition, and of specifying a noise generation site in the MRI apparatus, on the basis of a measurement time difference in the noise that is measured in the plurality of different sites.

Advantageous Effects of the Invention

According to the invention, it is possible to accurately specify a noise generation site in an MRI apparatus.

BRIEF DESCRIPTION OF THE DRAWINGS

FIG. 13 relates to a modification example of the noise source search device according to the first embodiment of the invention, and is a reference diagram in a case where a noise generation site is searched on the basis of a phase difference.

MODE FOR CARRYING OUT THE INVENTION

A noise generation source search device according to an embodiment of the invention is applied to an MRI apparatus that obtains an NMR signal generated from a subject disposed in a static magnetic field by applying an RF pulse of a high frequency coil and a gradient magnetic field pulse of a gradient magnetic field coil to the subject, and includes: a reference antenna and a probe antenna that measure a noise generated in the MRI apparatus; a noise generation condition specification unit that specifies a noise generation condition generated in the MRI apparatus, on the basis of a noise intensity of the noise that is measured by the reference antenna; and a noise generation site specification unit that measures a noise generated under the noise generation condition that is specified by the noise generation condition specification unit, with the reference antenna and the probe antenna disposed in a position different from that of the reference antenna, and specifies a noise generation site in the MRI apparatus, on the basis of a measurement time difference in the noise that is measured by the reference antenna and the probe antenna.

According to this embodiment, it is possible to accurately specify the noise generation site in the MRI apparatus.

Hereinafter, embodiments of the invention will be described with reference to the drawings.

The noise generation source search device specifies the noise source and the noise generation site with respect to the noise that is generated in the MRI apparatus, can be built in the MRI apparatus, and can be configured as an independent device.

The noise generation source search device according to each of the embodiments described below, for example, searches the noise source of the noise that is generated in the MRI apparatus illustrated in FIG. 1, that is, a noise generation condition and a noise generation site, and the MRI apparatus is configured as an independent device.

(Configuration of MRI Apparatus)

Figure 1:
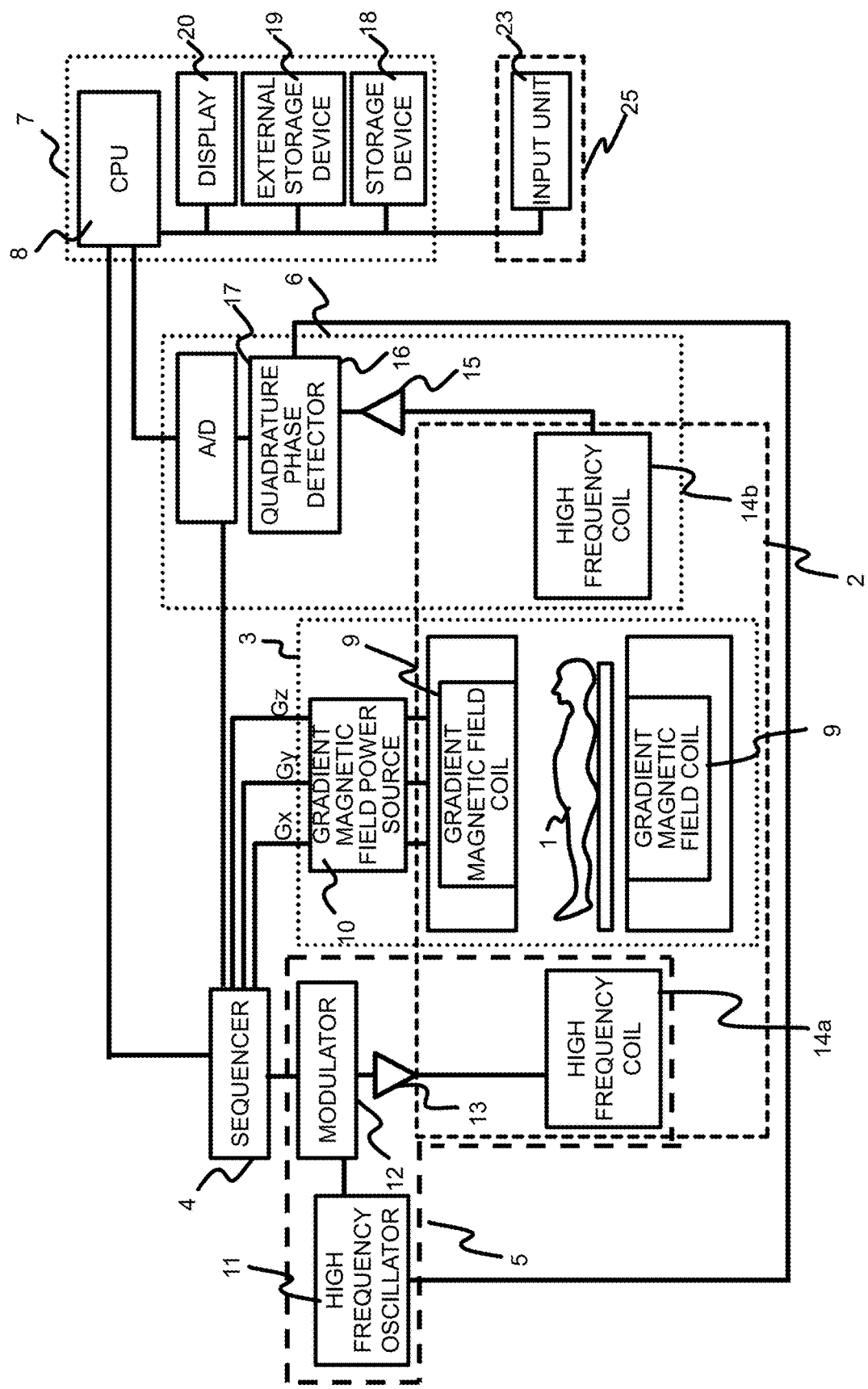
FIG. 1 is a block diagram illustrating a schematic configuration according to an example of an MRI apparatus that searches a noise source by a noise generation source search device according to a first embodiment of the invention.

The MRI apparatus illustrated in FIG. 1 includes a static magnetic field generation unit 2, a gradient magnetic field generation unit 3, a sequencer 4, a transmitting unit 5, a receiving unit 6, a signal processor 7, and a central processing unit (CPU) 8.

In the static magnetic field generation unit 2, a permanent magnet type static magnetic field generation source, a normal conduction type static magnetic field generation source, or a superconduction type static magnetic field generation source is disposed around a subject 1. In a case where the static magnetic field generation unit 2 is a vertical magnetic field type static magnetic field generation unit, a homogeneous static magnetic field is generated in a direction orthogonal to a body axis, in a space around the subject 1, and in a case where the static magnetic field generation unit 2 is a horizontal magnetic field type static magnetic field generation unit, a homogeneous static magnetic field is generated in a body axis direction.

The gradient magnetic field generation unit 3 includes gradient magnetic field coils 9 that apply a gradient magnetic field in directions of three axes of X, Y, and Z that are a coordinate system of the MRI apparatus (a coordinate system at rest), and a gradient magnetic field power source 10 that drives each of the gradient magnetic field coils 9. The gradient magnetic field power source 10 of each of the coils is driven in accordance with a command from the sequencer 4 described below, and thus, gradient magnetic fields Gx, Gy, and Gz are applied in the directions of three axes of X, Y, and Z.

At the time of photographing, a sliced surface with respect to the subject 1 is set by applying a slice direction gradient magnetic field pulse (Gs) in a direction orthogonal to a sliced surface (a photographic profile), and position information in each of the directions is encoded in an NMR signal by applying a phase encoding direction gradient magnetic field pulse (Gp) and a frequency encoding direction gradient magnetic field pulse (Gf) in two remaining directions that are orthogonal to the sliced surface and are orthogonal to each other.

The sequencer 4 controls the RF pulse and the gradient magnetic field pulse such that the RF pulse and the gradient magnetic field pulse are repeatedly applied in a predetermined pulse sequence. The sequencer 4 is operated under the control of the CPU 8 described below, and transmits various commands necessary for data collection of a tomographic image of the subject 1 to the transmission unit 5, the gradient magnetic field generation unit 3, and the reception unit 6.

The transmitting unit 5 irradiates the subject 1 with the RF pulse in order to cause nuclear magnetic resonance in an atomic nucleus spin of an atom configuring a body tissue of the subject 1, and includes a high frequency oscillator 11, a modulator 12, a high frequency amplifier 13, and a high frequency coil (a transmission coil) 14a on a transmission side. The RF pulse output from the high frequency oscillator 11 is subjected to amplitude modulation by the modulator 12 at a timing according to a command from the sequencer 4, and a high frequency pulse that is subjected to the amplitude modulation is amplified by the high frequency amplifier 13, and then, is supplied to the high frequency coil 14a that is disposed close to the subject 1, and thus, the subject 1 is irradiated with the RF pulse.

The receiving unit 6 detects the NMR signal that is emitted by the nuclear magnetic resonance of the atomic nucleus spin configuring the body tissue of the subject 1 (a nuclear magnetic resonance signal), and includes a high frequency coil (a reception coil) 14b on a reception side, a signal amplifier 15, a quadrature phase detector 16, and an A/D converter 17. The NMR signal of the response of the subject 1 induced by the RF pulse that is applied from the high frequency coil 14a on the transmission side is detected by the high frequency coil 14b that is disposed close to the subject 1, is amplified by the signal amplifier 15, and then, is divided into orthogonal diphyletic signals by the quadrature phase detector 16 at the timing according to the command from the sequencer 4, and each of the signals is converted into a digital amount by the A/D converter 17, and is sent to the signal processor 7 as measurement data.

The NMR signal of the response of the subject 1 induced by the RF pulse that is applied from the high frequency coil 14a on the transmission side is detected by the high frequency coil 14b that is disposed close to the subject 1, is amplified by the signal amplifier 15, and then, is divided into orthogonal diphyletic signals by the quadrature phase detector 16 at the timing according to the command from the sequencer 4, and each of the signals is converted into the digital amount by the A/D converter 17, and is sent to the signal processor 7 as the measurement data.

Note that, in FIG. 1, in a static magnetic field space of the static magnetic field generation unit 2 into which the subject 1 is inserted, the high frequency coil 14a on the transmission side and the gradient magnetic field coil 9 are provided to face the subject 1 in the case of the vertical magnetic field type static magnetic field generation unit, and are provided to surround the subject 1 in the case of the horizontal magnetic field type static magnetic field generation unit. In addition, the high frequency coil 14b on the reception side is provided to face the subject 1 or to surround the subject 1.

The signal processor 7 performs various data processings, and display, storage, and the like with respect to a processing result, and includes the CPU 8, a storage device 18 such as a RAM and a ROM, an external storage device 19 such as a magnetic disk and an optical disk, and a display 20 such as a CRT.

The CPU 8 controls the entire MRI apparatus. That is, the CPU 8 controls the sequencer 4 such that the subject 1 is irradiated with a high frequency magnetic field pulse along with the application of the gradient magnetic field pulse, and the tomographic image of the subject 1 is imaged by obtaining a plurality of NMR signals, in accordance with an imaging sequence based on an imaging condition that is input. In a case where data is input into the CPU 8 from the reception unit 6, in the CPU 8, processing such as signal processing and image reconfiguration is executed. The CPU 8 displays the obtained tomographic image of the subject 1 on the display 20, and records the obtained tomographic image in the storage device 18 or the external storage device 19.

An operation unit 25 inputs various control information items of the MRI apparatus or control information of the processing that is performed by the signal processor 7, and includes an input unit 23. One or a plurality of combinations of input devices such as a mouse, a keyboard, or a trackball can be applied as the input unit 23. In addition, the input unit 23 receives the input of the imaging condition from a user, and transmits the input imaging condition to the CPU 8.

The operation unit 25 is disposed close to the display 20, and thus, an operator is capable of interactively controlling various processings of the MRI apparatus through the operation unit 25 while watching the display 20.

First Embodiment

Figure 2:
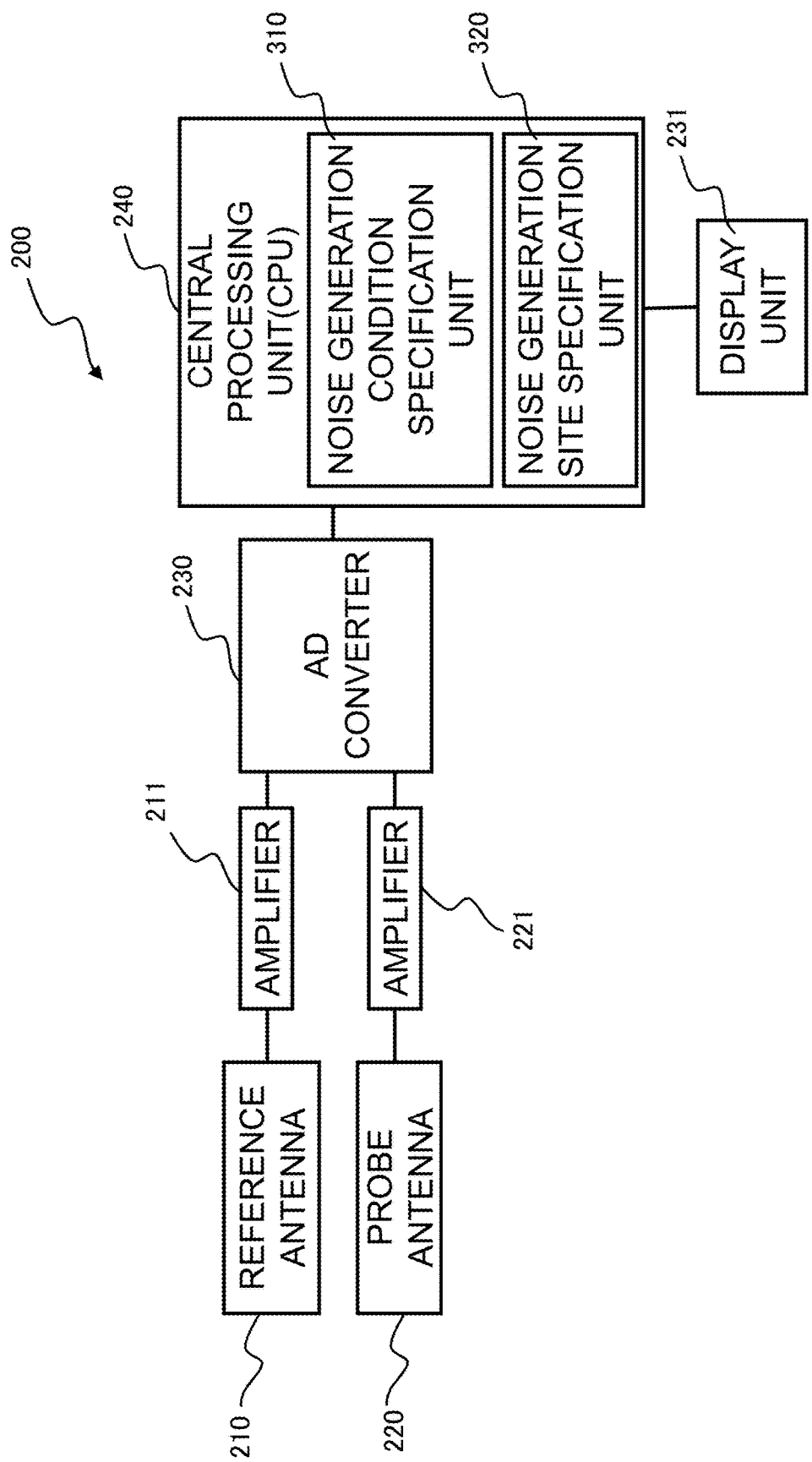
FIG. 2 is a block diagram illustrating a schematic configuration of the noise source search device according to the first embodiment of the invention.

As illustrated in FIG. 2, a noise generation source search device 200 according to a first embodiment of the invention includes a reference antenna 210, a probe antenna 220, amplifiers 211 and 221, an AD converter 230, a display unit 231, and a central processing unit (CPU) 240.

The reference antenna 210 measures a noise, and measures the noise by being fixed to a specific measurement position in the vicinity of the MRI apparatus, at the time of searching the noise source, in particular, at the time of specifying the noise generation site. A reception signal of the reference antenna 210 is used as a reference of the time difference or the noise intensity in the noise measurement described below.

The probe antenna 220 measures a noise as with the reference antenna 210, and detects a difference in time when a relative noise reaches the antenna or a difference in the noise intensity, in a relationship with respect to the reference antenna 210, while changing the measurement position, at the time of searching the noise source.

In particular, the probe antenna 220 is exposed to the static magnetic field or the gradient magnetic field in the vicinity of a bore of a gantry in the MRI apparatus, and thus, it is desirable that the probe antenna is an antenna that measures an electric field. Alternatively, in addition to the antenna that measures the magnetic field, an antenna to which a highpass type filter is added can be applied as the probe antenna 220. In FIG. 2, an example is illustrated in which the number of probe antennas 220 is one, but a plurality of probe antennas 220 can be provided. In this case, it is necessary to uniform the properties of the plurality of probe antennas (in particular, a cable length), but it is advantageous in that a measurement time can be shortened.

The amplifier 211 amplifies the noise that is measured by the reference antenna 210, and outputs the noise to the AD converter 230. Similarly, the amplifier 221 amplifies the noise that is measured by the probe antenna 220, and outputs the noise to the AD converter 230. The noise that is measured by the reference antenna 210 and the probe antenna 220 is a considerably weak signal, and thus, it is difficult to capture the noise with the AD converter as it is. Therefore, the amplifiers 211 and 221 are provided, and the amplified noise signal is output to the AD converter.

It is considered that the shot noise in the MRI apparatus is in the shape of an extremely short impulse, and thus, a broad frequency band is necessary in order to accurately measure a reach time. For this reason, it is desirable that frequency properties of the amplifiers 211 and 221 have a sensitivity and an amplification degree in a broad range.

The AD converter 230 converts the noise that is input from the amplifiers 211 and 221 into a digital noise signal, and outputs the signal to the display unit 231. The display unit 231 displays the digital noise signal that is input from the AD convertor 230 in a predetermined display type. For example, an oscilloscope can be applied as the AD converter 230 and the display unit 231.

The AD converter 230 measures a propagation delay of an electromagnetic wave in the vicinity of the MRI apparatus, and thus, resolution power in a time direction is strongly required. A delay while the electromagnetic wave proceeds 10 cm is 0.3 ns, and thus, such a degree of time resolution power is necessary for the AD converter 230.

The CPU 240 performs various processings such as analysis, on the noise signal that is measured by the reference antenna 210 and the probe antenna 220, and is converted into the digital signal by the AD converter 230. Although it is not illustrated, as necessary, the CPU includes a memory that is a working area at the time of the processing, and a storage unit storing data that is used in advance in necessary programs or processings, data that is generated in the processing, data that is obtained as a result of the processing, and the like. An analysis result of the CPU 240 is output to the display unit 231.

In this embodiment, as illustrated in FIG. 2, the CPU 240 includes a noise generation condition specification unit 310 and a noise generation site specification unit 320, and the generation condition and the noise source of the noise that is generated from the MRI apparatus (the noise generation site) are specified by each unit included in the CPU 240.

Note that, the CPU 240 reads and executes a program that is stored in advance in a predetermined storage device, and thus, the function of each unit included in the CPU 240 can be attained as software. In addition, a part or all of operations that are executed by each unit included in the CPU 240 can be attained by hardware such as an application specific integrated circuit (ASIC) or a field-programmable gate array (FPGA).

The noise generation condition specification unit 310 specifies the generation condition of the noise that is generated in the MRI apparatus, on the basis of the noise intensity of the noise that is measured by the reference antenna 210. In order to evaluate the size of the noise, the noise intensity is measured by the reference antenna 210, by driving each of the gradient magnetic field coils on X, Y, and Z axes of the MRI apparatus for a predetermined time while changing the drive frequency. Then, the noise generation condition specification unit 310 specifies the axis and the drive frequency of the gradient magnetic field coil when a noise indicating a noise intensity that exceeds a predetermined threshold value is generated, as the noise generation condition, from a measurement result.

In a case where the drive frequency of the gradient magnetic field coil is changed, not only the gradient magnetic field coil but also an irradiation coil configuring the MRI apparatus, small individual metal fittings included in each configuration, an electric component, and the like are subjected to the vibration. At this time, a natural vibration frequency in the vicinity of a member that generates a noise is coincident with the drive frequency, and a noise is generated as a result of the increased vibration. In order to detect such a noise, as described above, the gradient magnetic field coil of the MRI apparatus is driven for a predetermined time, and the noise is continuously measured by the reference antenna 210. Then, the noise generation condition specification unit 310 specifies the axis and the drive frequency of the gradient magnetic field coil at the time of indicating the noise intensity that exceeds a predetermined threshold, in the noise that is continuously measured by the reference antenna 210, as the noise generation condition.

Note that, a noise that requires the repeated drive of the gradient magnetic field coil is not generated by one-shot impulse, and thus, sweeping in a frequency direction in which the drive frequency is changed, but not the excitation in a broad band due to an impulse, is necessary. A waveform may be a sine curve or may be a trapezoidal wave, but it is necessary to ensure a sweeping time to some extent.

Note that, the noise generation due to not only each of the X, Y, and Z axes but also a combination of the respective axes is considered, but it is sufficient to consider linear addition, and it is not necessary to measure the noise by a combination.

An intensity direction is linear in a general dynamical system, but is non-linear in the problem of friction and contact-non-contact. It is desirable that a test is performed at the maximum intensity in an allowable range.

In a case where a noise is generated from a plurality of sites, a plurality of noise generation conditions, that is, a plurality of axes and a plurality of drive frequencies are considered.

Figure 3A:
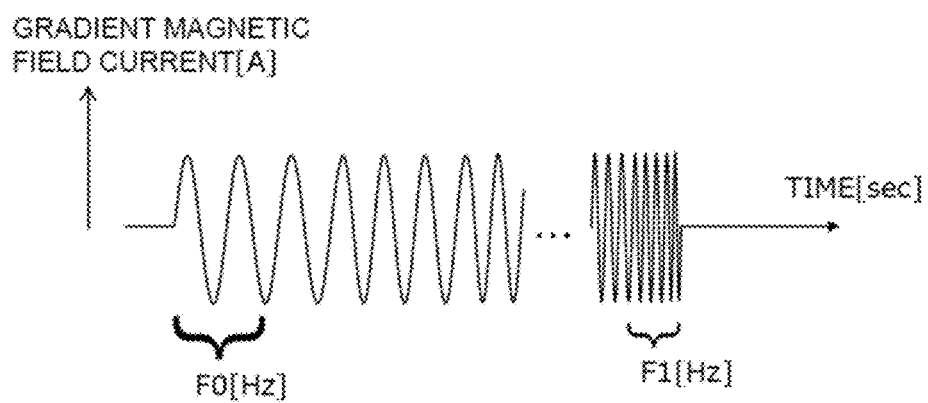
FIG. 3A is a graph showing a sweeping state of a drive frequency of a gradient magnetic field coil.
Figure 3B:
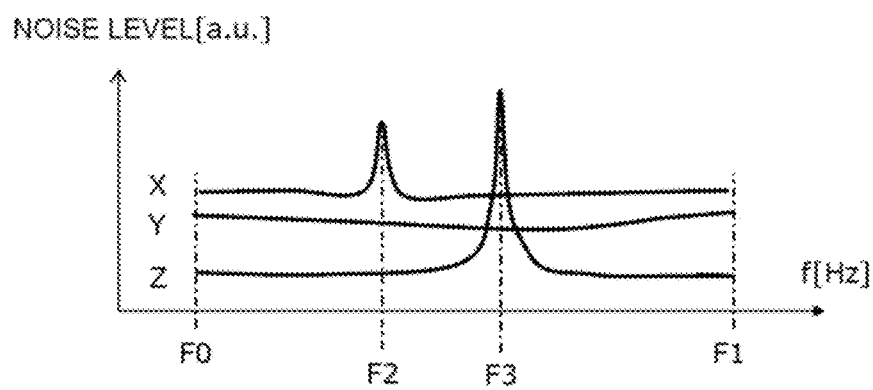
FIG. 3B is a graph showing a measurement result of a noise level that is measured by a reference antenna in the case of driving the gradient magnetic field coil while changing the drive frequency, in an MRI apparatus that searches a noise by the noise source search device according to the first embodiment of the invention.

More specifically, for example, the gradient magnetic field coil is swept while the drive frequency is changed from F0 [Hz] to F1 [Hz] (FIG. 3A). The noise generation condition specification unit 310 processes a measurement result of the reference antenna 210 at this time, and thus, a graph as shown in FIG. 3B is generated. In the example illustrated in FIG. 3B, it is seen that there are two frequencies with a great noise at F2 [Hz] on the X axis and F3 [Hz] on the Z axis. In this case, there is a possibility that each of F2 and F3 is the same or separate noise source, that is, the noise generation sites are different from each other, and thus, the noise generation sites are individually specified by the noise generation site specification unit 320.

Note that, in a case where F0 is excessively low, current output per an evaluation window time of the gradient magnetic field current excessively increases, and an extension in the sweeping time is caused, and thus, it is preferable to perform truncation at a suitable frequency. In addition, in a case where F1 is excessively high, the next eddy current is generated before an eddy current that is generated in accordance with an increase and a decrease in the pulse is eliminated, and there is a concern that eddy current heat generation becomes excessive, and thus, it is also necessary not to be a suitable frequency or more. In any case, it is necessary to select a suitable frequency for each type of device, in accordance with the specification of the gradient magnetic field power source configuring the MRI apparatus, the specification of the cooling of the gradient magnetic field coil, or the like.

The noise generation site specification unit 320 specifies the noise generation site in the MRI apparatus, on the basis of a reach time difference in the noise that is simultaneously received by the reference antenna 210, and the probe antenna 220 disposed in a position different from that of the reference antenna 210, on the basis of the noise generation condition that is specified by the noise generation condition specification unit 310.

Figure 4:
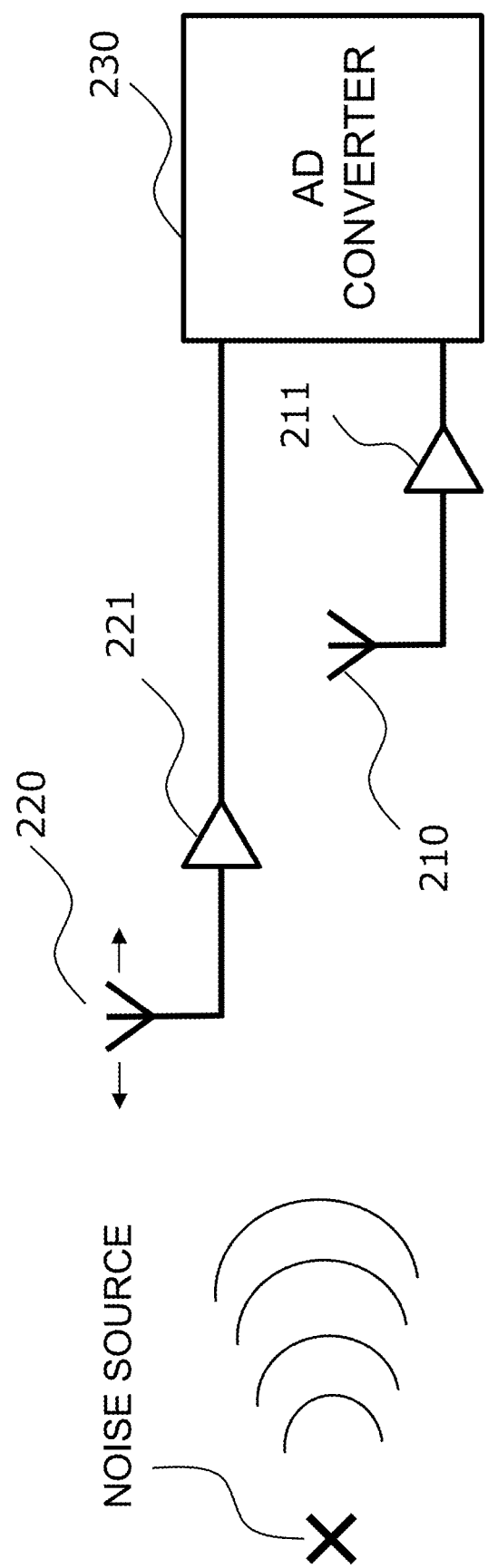
FIG. 4 is a reference diagram illustrating a state in which the reference antenna and a probe antenna measure a noise that propagates through the air as an electromagnetic wave, in the noise source search device according to the first embodiment of the invention.
Figure 5:
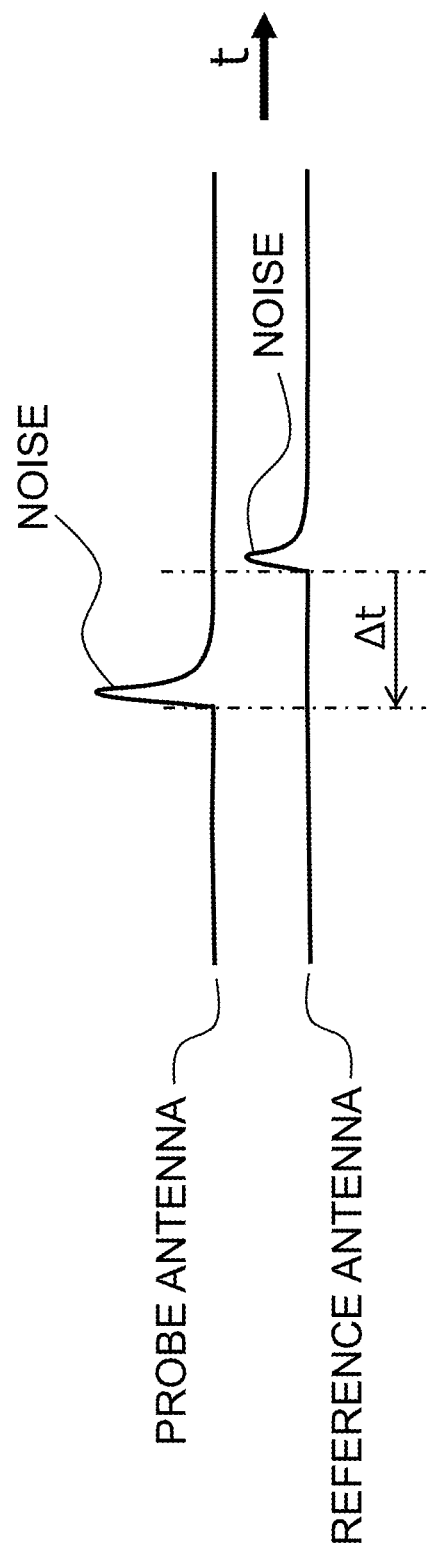
FIG. 5 is an example of a graph showing a noise measurement result of a reference antenna 210 and a probe antenna 110, in the noise source search device according to the first embodiment of the invention.

As illustrated in FIG. 4, in a case where a noise is generated in the noise source, the noise propagates through the air as an electromagnetic wave, and is captured by the reference antenna 210 and the probe antenna 220. The noise that is captured by two antennas is amplified by each of the amplifiers 211 and 221, is input into the AD converter 230 through a cable, is converted into a digital signal, and then, is input into the noise generation site specification unit 320. Then, the noise generation site specification unit 320 acquires a time difference ($\Delta t$) at which the noise reaches both of the antennas from a measurement result of the reference antenna 210 and a measurement result of the probe antenna 220 (refer to FIG. 5). In a case where the time difference ($\Delta t$) is repeatedly acquired by repeating the measurement while moving the probe antenna 220, and time differences are plotted, for example, it is possible to obtain a graph shown in FIG. 6.

The reference antenna 210 is in a position separated from the probe antenna 220, the time difference $\Delta t$ increases as the probe antenna 220 is close to the noise source, and in a case where the probe antenna 220 is separated from the noise source, $\Delta t$ decreases again, and thus, it is possible to consider that a location in which the time difference is maximized is closest to the noise source. That is, in the graph of FIG. 6, a location in which the time difference $\Delta t$ indicates a local maximum value is considered as the vicinity of the noise source. Accordingly, the noise generation site specification unit 320 calculates the measurement time difference, on the basis of the measurement result of the reference antenna 210 and the probe antenna 220, performs the measurement while changing the position of the probe antenna 220, and specifies the noise source from a plurality of measurement time differences or noise intensity differences.

Figure 7:
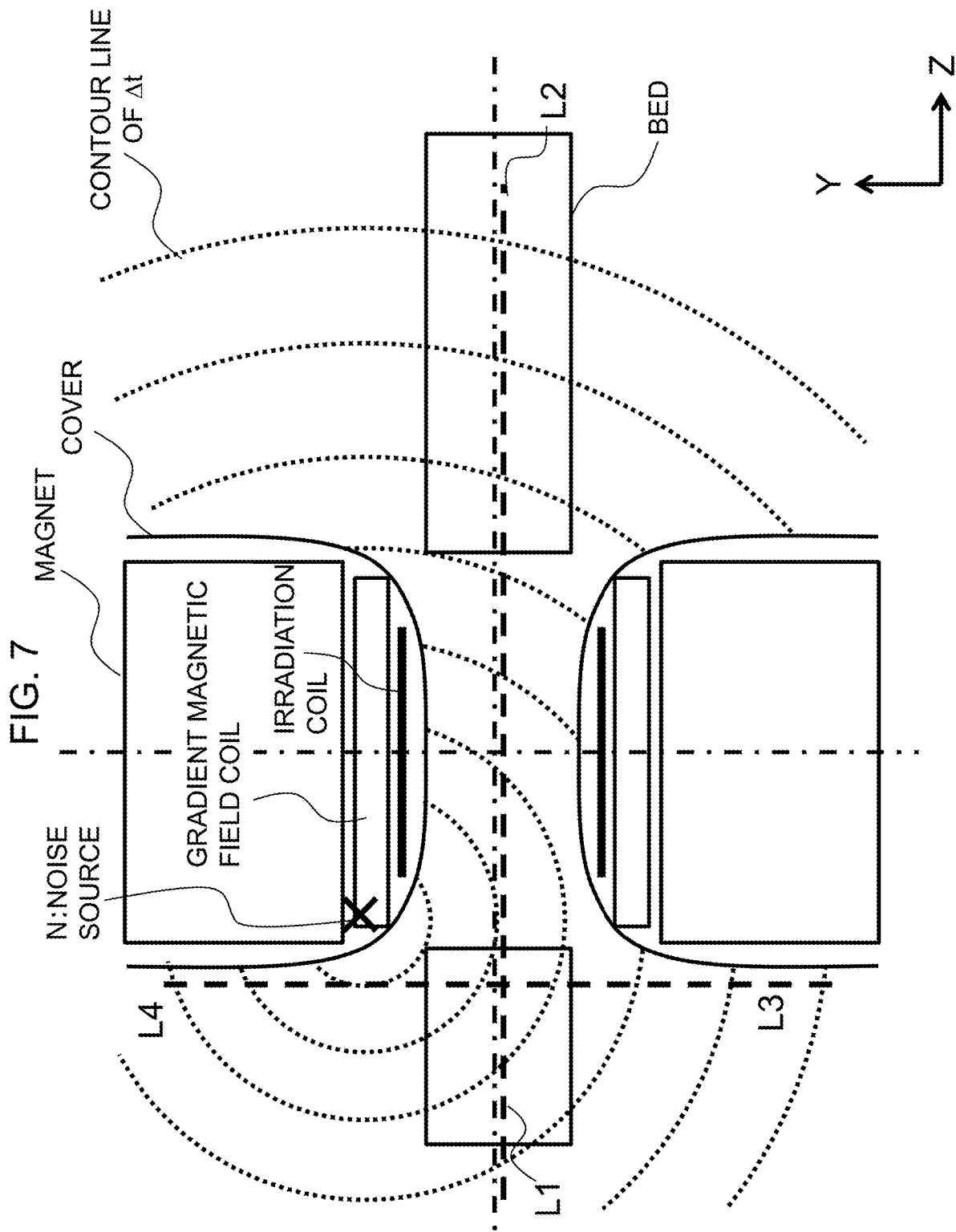
FIG. 7 is a schematic view of a measurement example with respect to a three-dimensional location in a case where the noise source is searched by the noise source search device according to the first embodiment of the invention.
Figure 8:
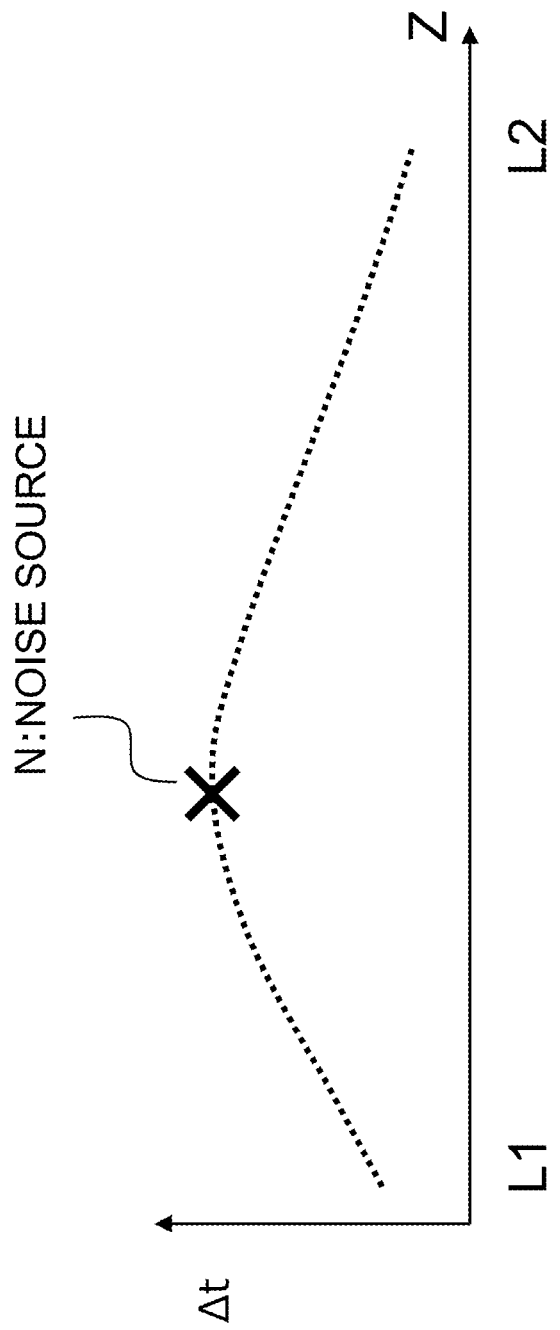
FIG. 8 is a schematic view of a measurement example with respect to the three-dimensional location in a case where the noise source is searched by the noise source search device according to the first embodiment of the invention.
Figure 9:
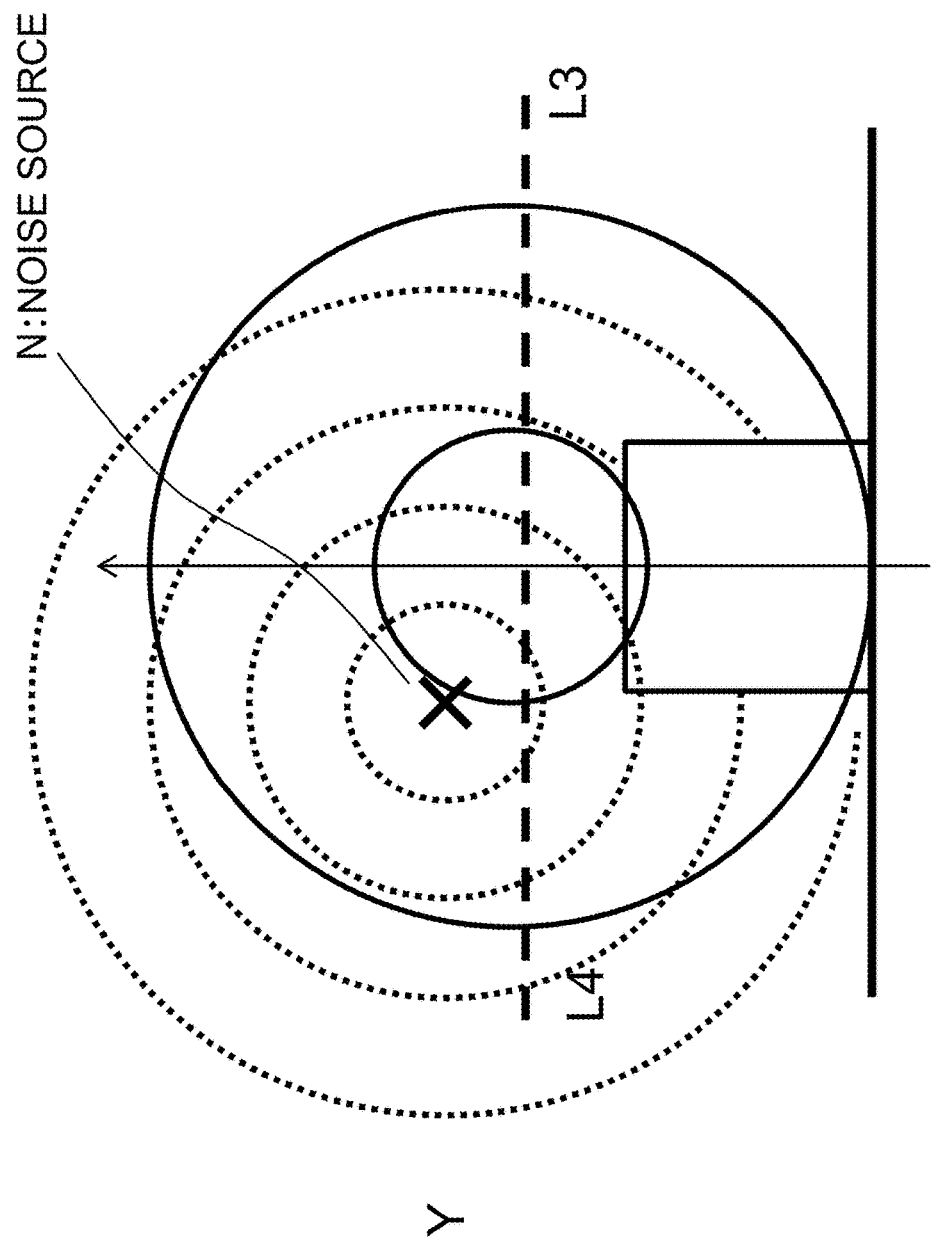
FIG. 9 is a schematic view of a measurement example with respect to the three-dimensional location in a case where the noise source is searched by the noise source search device according to the first embodiment of the invention.

In practice, it is necessary to perform measurement with respect to a three-dimensional location. In FIG. 7 to FIG. 9, a schematic view of a measurement example is illustrated. In a case where N illustrated in FIG. 7 is set to the noise source, a method of specifying the noise source will be described.

First, a noise is measured by the reference antenna 210 and the probe antenna 220, along a z axis in FIG. 7 and a straight line L1-L2 in FIG. 7, and the time difference $\Delta t$ is calculated by the noise generation site specification unit. As illustrated in FIG. 8, the time difference $\Delta t$ draws a curve having a local maximum value (or a local minimum value) at an arbitrary site. From such a result, it is assumed that there is a noise source closer to a side opposite to a bed than in front of the gantry (the bed side) or in a patient bore. Next, for example, the time difference $\Delta t$ is two-dimensionally plotted on a plane including L3-L4. Then, as illustrated in FIG. 9, it is possible to draw a contour line that specifies a location such as a right side of the MRI apparatus when seen from behind and an area along the inner edge of the bore.

As described above, the location may be specified in sequence, or three-dimensionally data may be acquired. Alternatively, measurement of narrowing down the details after roughly specifying the location may be performed. In addition, the noise source is not limited to one site, and thus, it is preferable to cyclopaedically specify the axis and the frequency of the gradient magnetic field coil that are specified by the frequency sweeping described above.

The flow of noise source search processing in the noise source search device 200 configured as described above will be described in accordance with flowcharts of FIG. 10 to FIG. 12.

Figure 10:
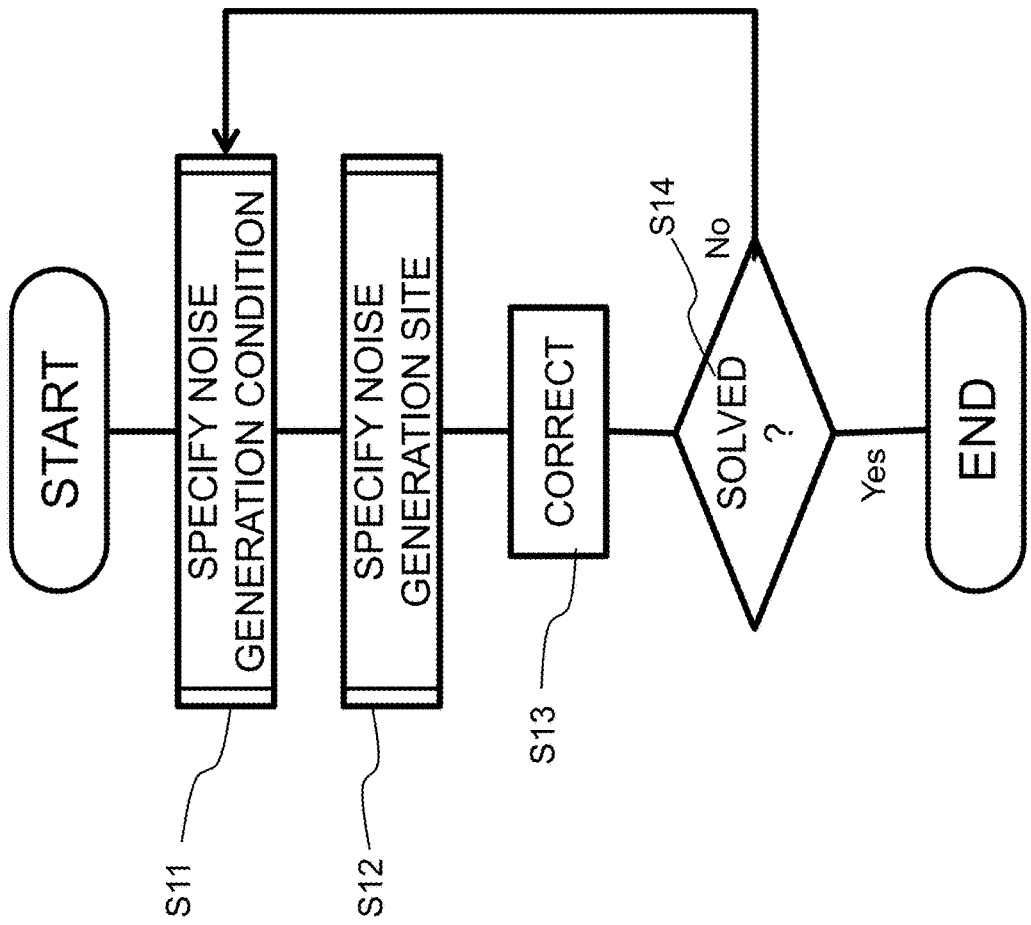
FIG. 10 is a flowchart illustrating a flow of noise source search processing of the noise source search device according to the first embodiment of the invention.

As illustrated in FIG. 10, in Step S11, the axis and the drive frequency of the gradient magnetic field coil in the MRI apparatus are specified by the noise generation condition specification unit 310, as the noise generation condition. Subsequently, in Step S12, the gradient magnetic field coil is driven with the axis and the drive frequency that are specified in Step S11, and the noise generation site is specified. The flow of noise generation condition specification processing and the flow of noise generation site specification processing will be described below.

In Step S13, the noise source search device 200 provides an opportunity for correcting the noise generation site of the MRI apparatus to the user, and it is determined whether or not the noise is eliminated, from Step S14. In a case where the noise is not eliminated, the process from the specification of the noise generation condition is repeated again.

Note that, the specification of the noise generation condition is essential in a case where a noise generation frequency is high or a noise is generated from a plurality of sites, but can be omitted in a case where the noise generation frequency is low. Here, a case where the noise generation frequency is low is a case where one great noise is generated in several tens of slices, for example.

(Noise Generation Condition Specification Processing)

Next, the noise generation condition specification processing will be described.

Figure 11:
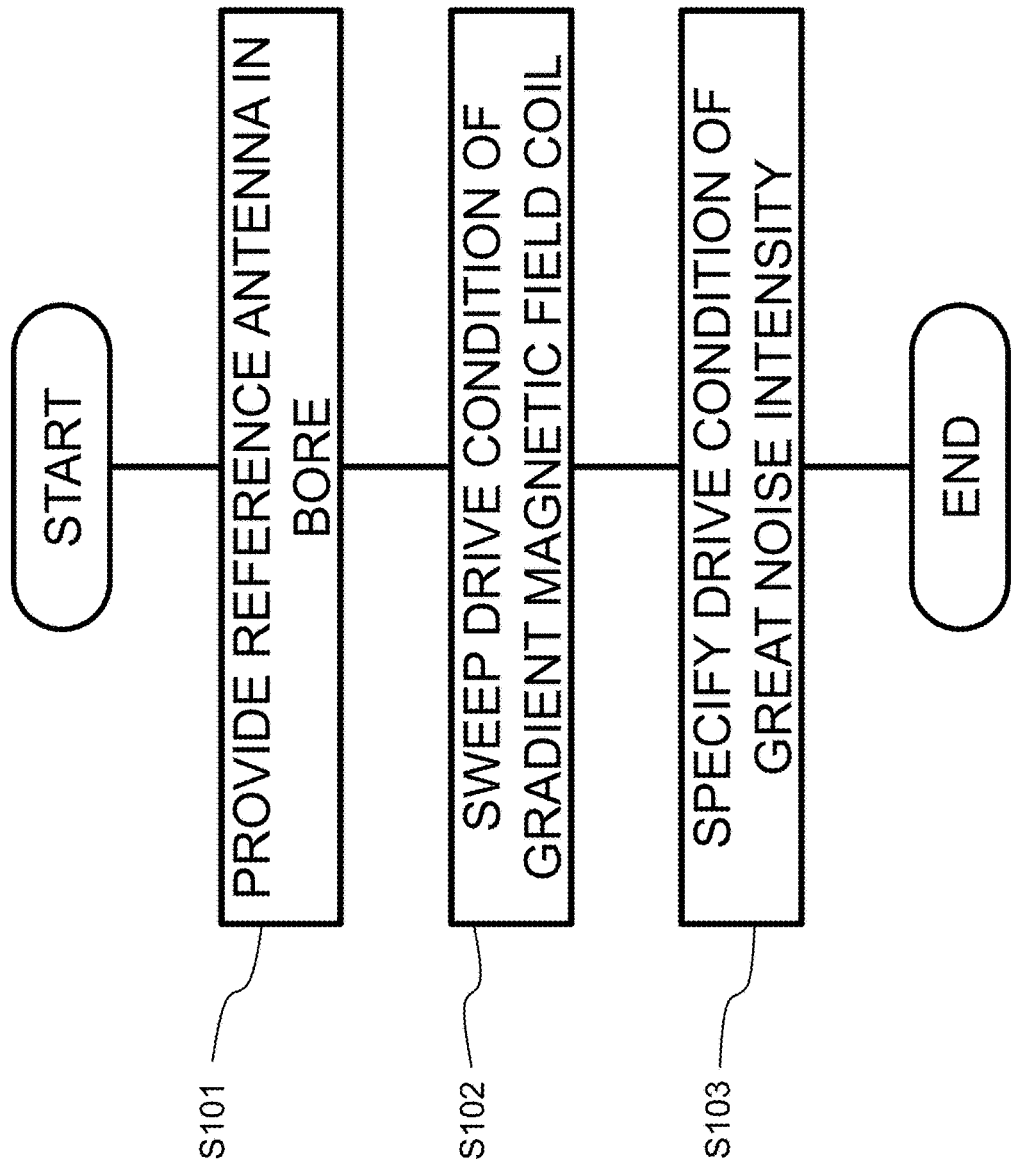
FIG. 11 is a flowchart illustrating a flow of noise generation condition specification processing of the noise source search device according to the first embodiment of the invention.
Figure 12:
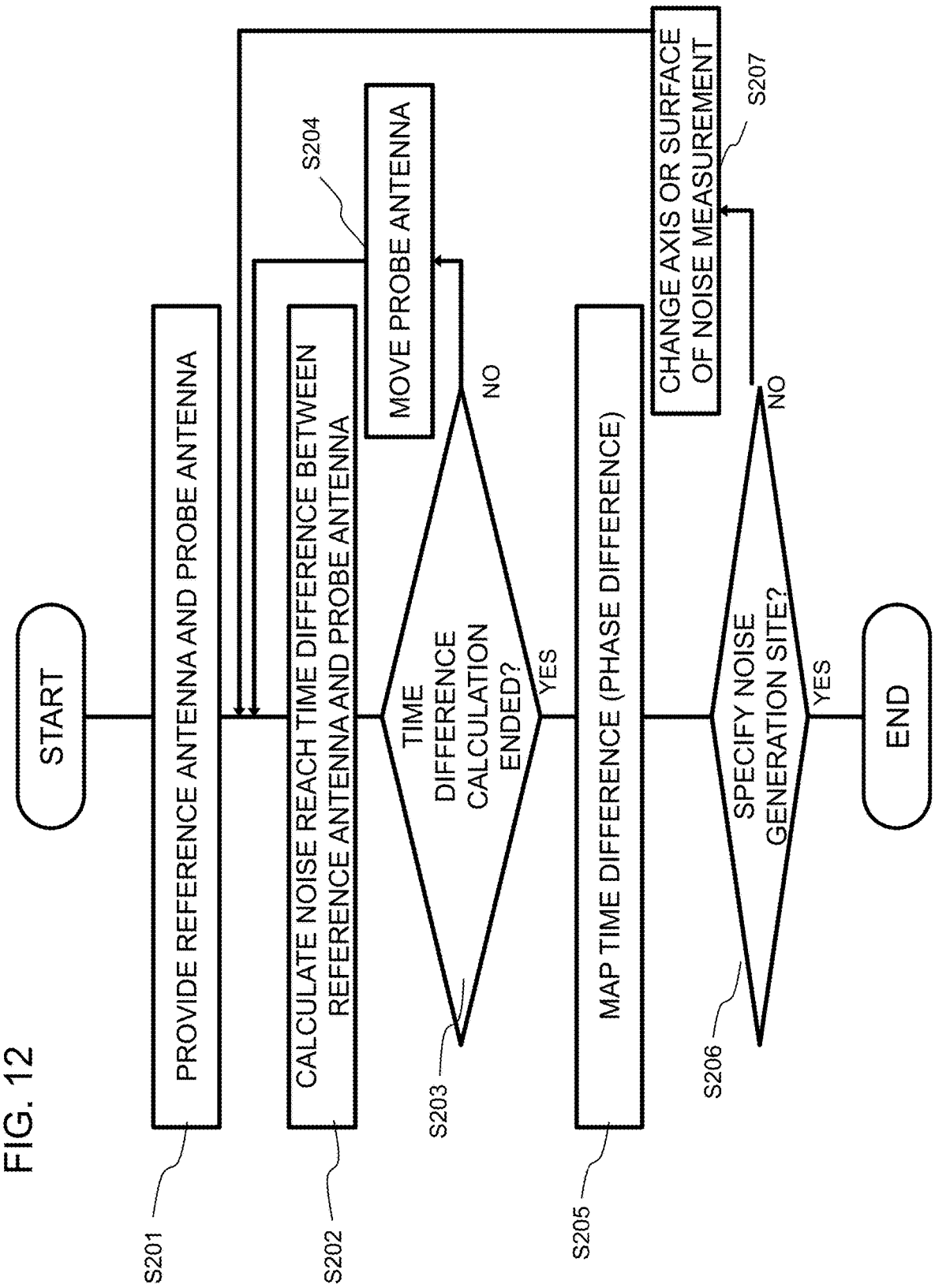
FIG. 12 is a flowchart illustrating a flow of noise generation site specification processing of the noise source search device according to the first embodiment of the invention.

As illustrated in FIG. 11, in order to evaluate the size of a noise, the reference antenna 210 is provided in the bore of the MRI apparatus (Step S101), and each of the gradient magnetic field coils is driven on the X, Y, and Z axes of the MRI apparatus for a predetermined time while the drive frequency is changed, and thus, the noise intensity is measured by the reference antenna 210 (Step S102). Then, the axis and the drive frequency of the gradient magnetic field coil when the noise indicating the noise intensity that exceeds a predetermined threshold value is generated are specified as the noise generation condition, from the measurement result (Step S103).

(Noise Generation Site Specification Processing)

Subsequently, the noise generation site specification processing will be described.

The gradient magnetic field coil is driven with the axis and the drive frequency according to the noise generation condition that are specified by the noise generation condition specification unit described above, and as illustrated in FIG. 12, the reference antenna 210 is fixed to a predetermined position in the bore of the MRI apparatus, and the probe antenna 220 is disposed in a predetermined position (Step S201). The noise is measured by the reference antenna 210 and the probe antenna 220, the time difference in the noise that is simultaneously received by the reference antenna 210 and the probe antenna 220 is calculated by the noise generation site specification unit 320, on the basis of the measurement result of the reference antenna 210 and the probe antenna 220 (Step S202).

In next Step S203, it is determined whether or not the measurement of the noise and the calculation of the time difference are performed as set in advance or sufficiently, and in a case where it is determined that the calculation is not performed, the process proceeds to Step S204, the probe antenna 220 is moved, the process returns to Step S202, and the noise is continuously measured by the reference antenna 210 and the probe antenna 220, and the time difference is continuously calculated by the noise generation site specification unit 320.

Figure 6:
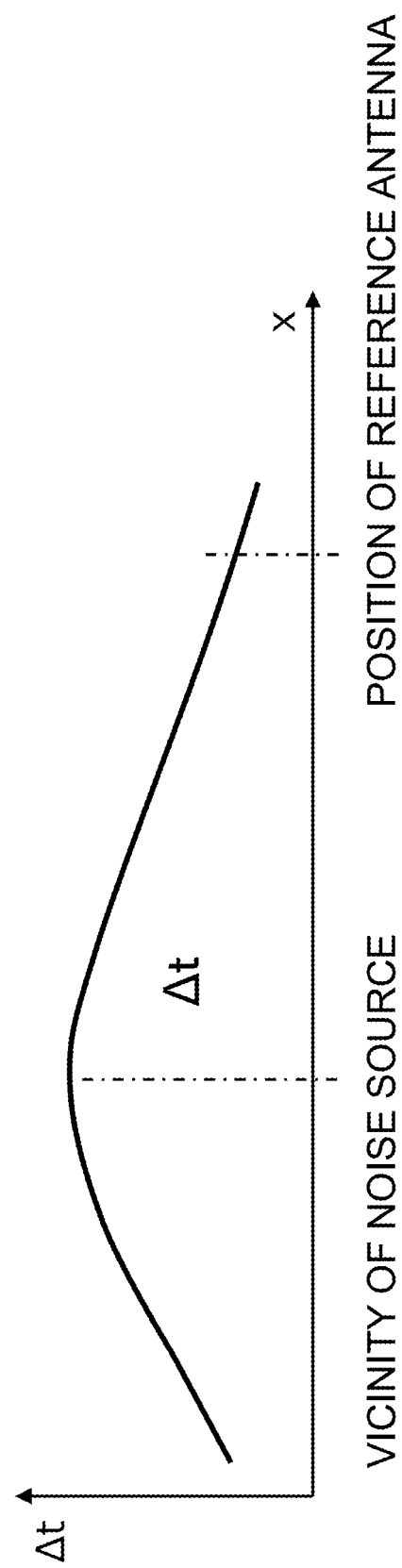
FIG. 6 is an example of a graph in which a plurality of time differences calculated from the noise measurement result of the reference antenna 210 and the probe antenna 220 are plotted, in the noise source search device according to the first embodiment of the invention.

In the determination of Step S203, in a case where it is determined that the noise measurement is sufficiently ended, the process proceeds to Step S205, and the time difference that is calculated by the noise generation site specification unit 320 is mapped. Here, for example, as shown in FIG. 6, a graph showing a relationship between the position of the antenna and the time difference is generated. Subsequently, the process proceeds to Step S206, and it is determined whether or not the noise source is specified, with reference to a mapping result. In the determination of Step S206, in a case where it is determined that the noise generation site is not specified, the process proceeds to Step S207, an axis or a surface on which the noise measurement is performed is changed, that is, a straight line (an axis) or a surface on which the probe antenna 220 is moved is changed, with reference to the mapping result, the process returns to Step S202, the measurement is performed while the position of the probe antenna 220 is changed again along the changed straight line or surface, and the time difference is calculated. In the determination of Step S206, in a case where it is determined that the noise generation site is specified, this processing is ended.

As described above, according to this embodiment, the axis and the drive frequency of the gradient magnetic field coil that generates a noise in the MRI apparatus are specified, and then, a site in which the noise is generated is searched, and thus, it is possible to accurately and circumstantially specify the noise generation site.

Note that, the time difference described above is proportional to a distance between the noise source and the antenna, but the noise intensity attenuates in proportion to the square of the distance. By using such a relationship, the noise generation site is searched to some extent, on the basis of the time difference, and then, the distribution of the noise intensity is acquired, and thus, it is possible to more circumstantially and reliably specify the noise generation site.

In addition, when the gradient magnetic field coil is driven in order to search the noise source, the drive of the gradient magnetic field coil may be attained by driving the MRI apparatus itself, or a drive device such as a pulse generator is further provided in the noise source search device, and the gradient magnetic field coil may be driven by using the pulse generator with a predetermined axis and a predetermined drive frequency.

Modification Example

In the first embodiment described above, an example has been described in which the noise generation site is specified on the basis of the noise reach time difference. However, the pulse of the actual noise is a considerably short impulse, and thus, in order to accurately detect the noise, expensive antenna, amplifier, and AD converter are necessary. Accordingly, in order to attain a less expensive noise generation source search device, it is possible to specify the noise generation site, on the basis of a phase difference (refer to FIG. 13). In this case, a narrowband antenna may be applied to the reference antenna and the probe antenna.

A range in which the noise generation site is searched is approximately 3 m to 10 m, and the reach time difference of the electromagnetic wave in the range is approximately 10 ns to 30 ns. Therefore, a wavelength at which a phase difference of 360 degrees is 10 ns to 30 ns is 100 MHz to 33 MHz, and in the case of a higher frequency, the phase is excessively rotated, and in a case where phase unwrapping processing is not performed, a correct phase difference is not capable of being obtained, and a lot of troubles on analysis occur. In contrast, in a case where the frequency is low, the phase difference decreases, and thus, detection resolution power is degraded. Therefore, it is preferable to search a suitable frequency in the range of approximately 30 MHz to 100 MHz.

(Number of Probe Antennas)

In the first embodiment and the modification example described above, an example using two antennas of the reference antenna and the probe antenna has been described. In the case of using two antennas of the reference antenna and the probe antenna, the noise generation site is specified by searching the local maximum (the local minimum) of a relative time difference in both of the antennas, and thus, it is not necessary that the reference antenna and the probe antenna are the same.

Figure 14:
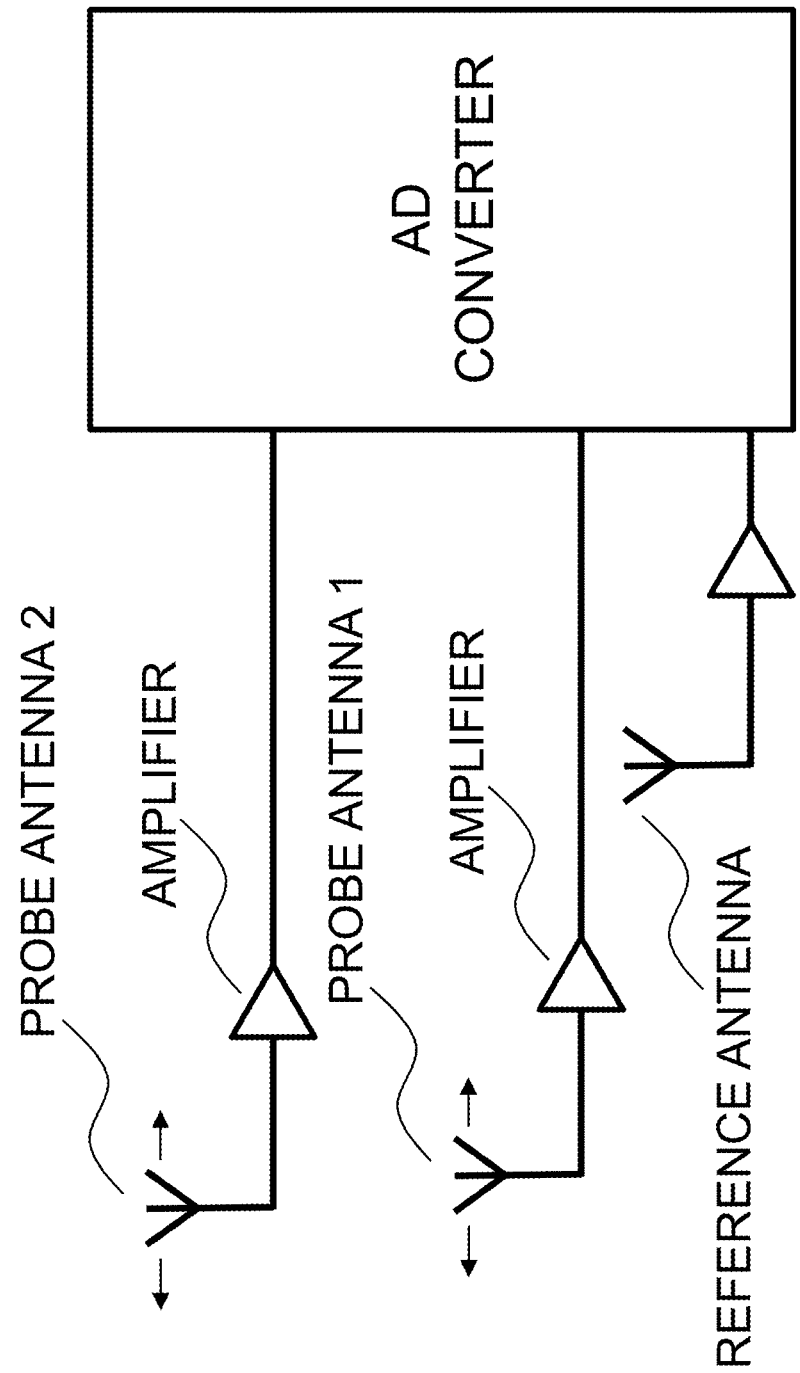
FIG. 14 relates to a modification example of the noise source search device according to the first embodiment of the invention, and is a reference diagram illustrating a state in which the reference antenna and two probe antennas measure the noise that propagates through the air as the electromagnetic wave.
Figure 15:
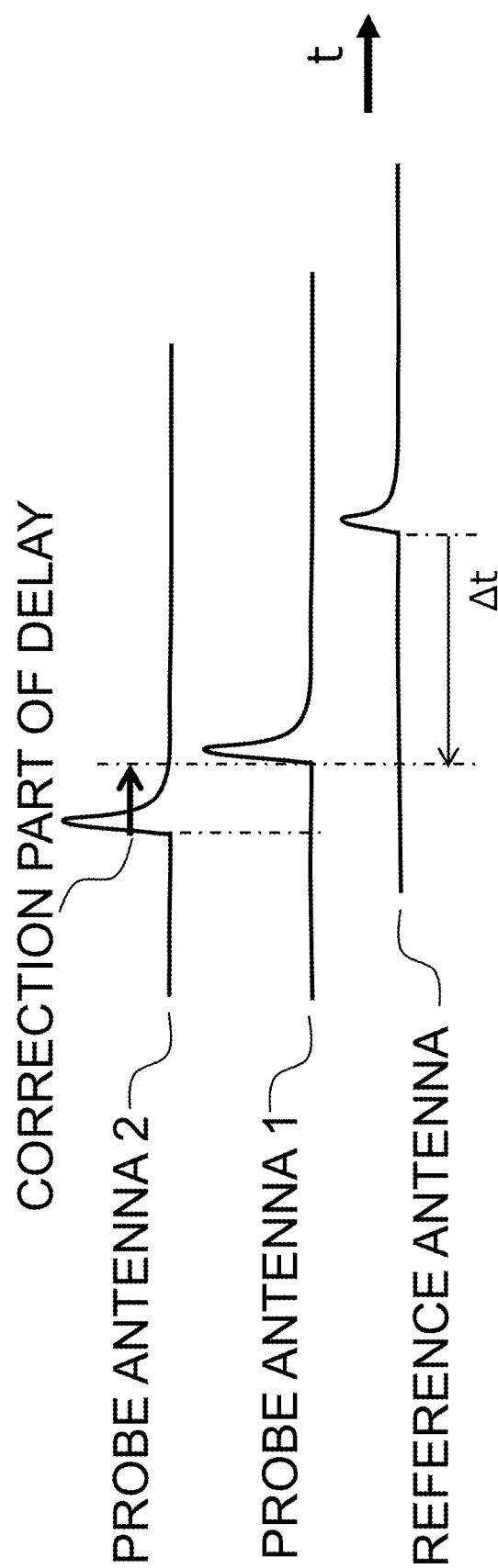
FIG. 15 relates to a modification example of the noise source search device according to the first embodiment of the invention, and is an example of a graph showing a noise measurement result of the reference antenna and two probe antennas.

However, in order to improve a measurement efficiency, it is preferable to increase the number of probe antennas (refer to FIG. 14 and FIG. 15). In this case, in a case where the properties of the plurality of probe antennas are different, it is not possible to accurately plot the time difference. For this reason, it is preferable that prior to the noise measurement, the probe antennas are disposed in the same location, $\Delta t$ with respect to a noise that is intentionally generated is measured, and a difference in the probes is calibrated. The calibration can be attained by subtracting the time difference after being measured, or by mechanically adjusting an electric length of the cable.

(Movement Method of Probe Antenna)

$\Delta t$ in each of the locations can be measured by automatically moving the probe antenna. Simply, $\Delta t$ can be measured by disposing the probe antenna on a top board that is moved along the z axis, and by moving the probe antenna along the z axis. Alternatively, the probe antenna may be disposed on a tip end of a jig that arbitrarily measures a cylindrical coordinate system of the z axis, r, and θ, and automatic measurement may be performed. Alternatively, a rod-like object may be operated from a wall surface that is separated from the gantry, and the probe antenna may be disposed in an arbitrary location. As described above, it is possible to improve the measurement efficiency of the noise, and thus, it is possible to improve the efficiency of the noise source search processing.

Second Embodiment

In the example described above, an example has been described in which the noise generation site is specified on the basis of the reach time difference or the intensity difference of the noise that is measured by using two antennas. In this embodiment, the antenna is disposed in four known locations, and the noise reach time difference in each of the locations is measured.

Figure 16:
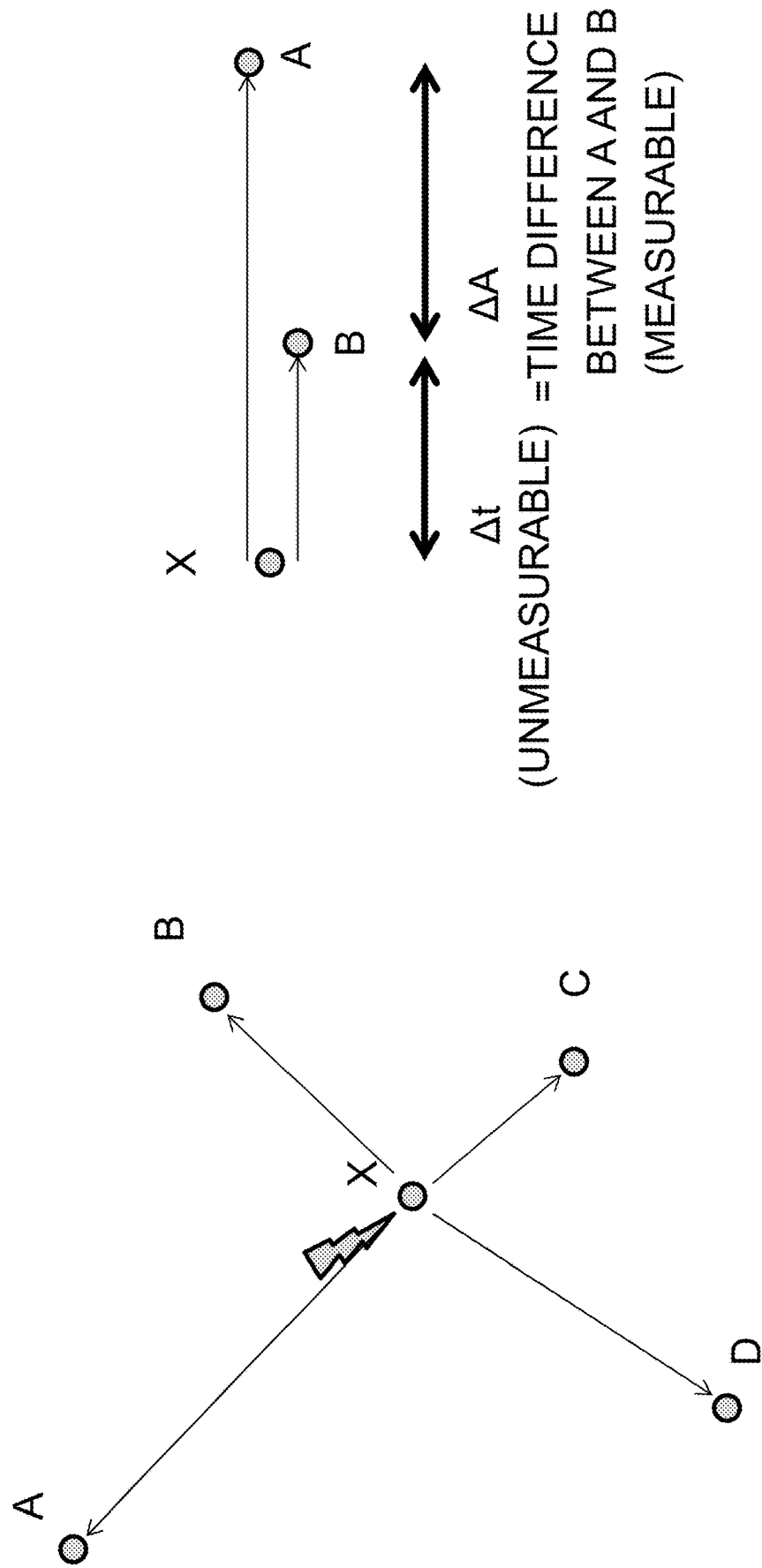
FIG. 16 is an explanatory diagram according to an example in which an antenna is disposed in four known locations, and a noise reach time difference in each of the locations is measured, in a noise source search device according to a second embodiment of the invention.
Figure 17B:
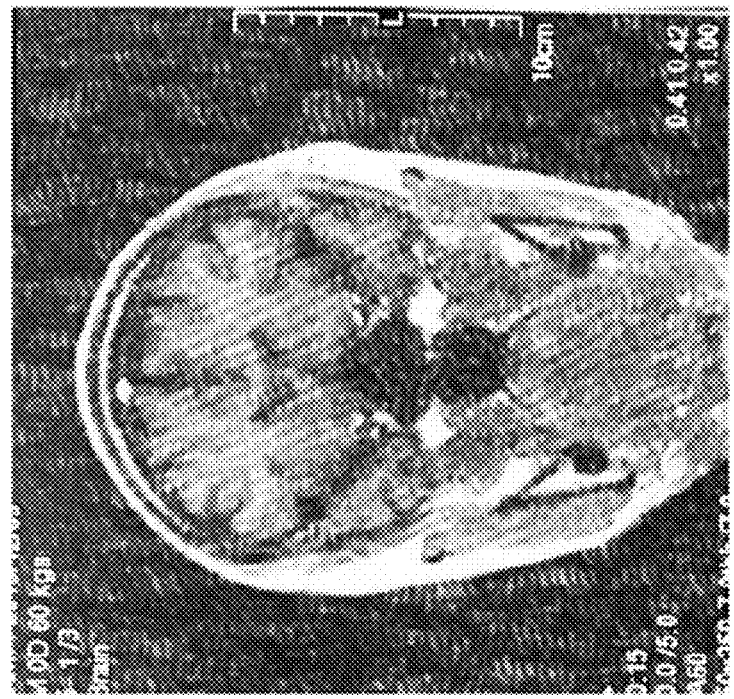
FIG. 17B is a reference diagram illustrating an example of the shot noise signal in a case where the K space data of FIG. 17A is changed to a real space image.
Figure 17A:
FIG. 17A is a reference diagram illustrating an example of a shot noise signal in K space data.

As illustrated in FIG. 16, in a case where an antenna position in four known sites is represented as (Vector A), (Vector B), (Vector C), and (Vector D), the noise source is represented as (Vector X), and the time difference that is measured in each of the locations is represented as $\Delta A$, $\Delta B$, $\Delta C$, and $\Delta D$, a relationship in the respective vectors can be represented as follows.

$$|(\text{Vector } A)-(\text{Vector } X)|=(\Delta A+\Delta t)*c$$

$$|(\text{Vector } B)-(\text{Vector } X)|=(\Delta B+\Delta t)*c$$

$$|(\text{Vector } C)-(\text{Vector } X)|=(\Delta C+\Delta t)*c$$

$$|(\text{Vector } D)-(\text{Vector } X)|=(\Delta D+\Delta t)*c$$

$\Delta A$ to $\Delta D$, in practice, measure a difference with respect to an antenna that is a reference but not measure a reach time from the noise source, and thus, there is a constant shift of $\Delta t$ in time required for the actual reach, regardless of a measurement point. c is a velocity at which the noise propagates through the air. Four unknowns with respect to four expressions described above are three coordinates configuring the vector X and $\Delta t$, and thus, can be solved numerically.

Note that, it is not necessary to simultaneously acquire four data sets, and in a case where the measurement is performed by two antennas, and three time differences are measured by moving one antenna, the measurement is performed on four sites, and thus, the noise source can be specified on the basis of the data.

REFERENCE SIGNS LIST

2 Static magnetic field generation unit
3 Gradient magnetic field generation unit
4 Sequencer
5 Transmitting unit
6 Receiving unit
7 Signal processor
8 Central processing unit (CPU)
9 Gradient magnetic field coil
10 Gradient magnetic field power source
11 High frequency oscillator
12 Modulator
13 High frequency amplifier
14a, 14b High frequency coil
15 Signal amplifier
16 Quadrature phase detector
17 A/D converter
18 Storage device
19 External storage device
20 Display
23 Input unit
25 Operation unit
210 Reference antenna
220 Probe antenna
211 Amplifier
221 Amplifier
230 AD converter
231 Display unit
240 Central processing unit (CPU)
310 Noise generation condition specification unit
320 Noise generation site specification unit

The invention claimed is:

1. A noise source search device to be applied to an MRI apparatus that obtains an NMR signal generated from a subject disposed in a static magnetic field by applying an RF pulse of a high frequency coil and a gradient magnetic field pulse of a gradient magnetic field coil to the subject, the device comprising:

a reference antenna and a probe antenna that measure a noise generated in the MRI apparatus;

a noise generation condition specification unit that specifies a noise generation condition generated in the MRI apparatus, on the basis of a noise intensity of the noise that is measured by the reference antenna; and a noise generation site specification unit that measures a noise generated under the noise generation condition that is specified by the noise generation condition specification unit, with the reference antenna and the probe antenna disposed in a position different from that of the reference antenna, and specifies a noise generation site in the MRI apparatus, on the basis of a measurement time difference in the noise that is measured by the reference antenna and the probe antenna.

2. The noise source search device according to claim 1, wherein the noise generation condition is an axis and a drive frequency of the gradient magnetic field coil.

3. The noise source search device according to claim 2, wherein the noise generation condition specification unit drives the gradient magnetic field coil on each of X, Y, and Z axes for a predetermined time, while changing the intensity and the drive frequency, and in a case where the noise intensity of the noise measured by the reference antenna exceeds a predetermined threshold value, specifies the axis and the drive frequency of the gradient magnetic field coil at the time of generating the noise indicating the noise intensity, as the noise generation condition.

4. The noise source search device according to claim 2, wherein the gradient magnetic field coil is driven in accordance with the axis and the drive frequency that are the noise generation condition specified by the noise generation condition specification unit,
the noise is measured by the reference antenna and the probe antenna while a measurement position of the reference antenna is fixed and a measurement position of the probe antenna is changed, and
the noise generation site specification unit calculates the measurement time difference or a noise intensity difference from a measurement result of the reference antenna and the probe antenna, and specifies the noise generation site, on the basis of the measurement time difference or the noise intensity difference.

5. The noise source search device according to claim 2, further comprising:
a pulse generator that drives the gradient magnetic field coil,
wherein the gradient magnetic field coil is driven by the pulse generator, in accordance with the axis and the drive frequency that are specified as the noise generation condition.

6. The noise source search device according to claim 1, wherein the measurement time difference is calculated from a difference in time when the same noise reaches the reference antenna and the probe antenna.

7. The noise source search device according to claim 1, wherein the measurement time difference is calculated by a phase difference in noise waveforms that are measured by the reference antenna and the probe antenna.

8. The noise source search device according to claim 1, further comprising:
an AD converter that receives input of a measurement result of the reference antenna and the probe antenna, and performs AD conversion with respect to the measurement result,
wherein the AD converter has time resolution power of 0.3 ns or less.

9. The noise source search device according to claim 1, wherein the probe antenna is an antenna that senses an electric field.

10. The noise source search device according to claim 1, wherein the probe antenna selectively senses a specific frequency.

11. The noise source search device according to claim 10, wherein the frequency is two times or more a resonance frequency of the MRI apparatus.

12. The noise source search device according to claim 10, wherein the frequency is 30 MHz to 100 MHz.

13. A noise source search method to be applied to an MRI apparatus that obtains an NMR signal generated from a subject disposed in a static magnetic field by applying an RF pulse of a high frequency coil and a gradient magnetic field pulse of a gradient magnetic field coil to the subject, the method comprising:
a noise generation condition specification step of measuring a noise generated from the MRI apparatus, and of specifying an axis and a drive frequency of the gradient magnetic field coil as a noise generation condition, on the basis of a noise intensity of the measured noise;
a step of measuring the noise generated from the MRI apparatus in a plurality of sites that are different from each other;
a noise generation site specification step of driving the gradient magnetic field coil, in accordance with the noise generation condition, and of specifying a noise generation site in the MRI apparatus, on the basis of a measurement time difference in the noise that is measured in the plurality of different sites.

* * * * *